United States Patent
DeVries et al.

(10) Patent No.: US 6,656,109 B2
(45) Date of Patent: Dec. 2, 2003

(54) SUCTION RETRACTOR FOR ATTACHING TO AN ORGAN WITHIN A BODY

(75) Inventors: James H. DeVries, Grand Rapids, MI (US); Steven R. Gundry, Redlands, CA (US); Brian S. Beals, East Grand Rapids, MI (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/837,270

(22) Filed: Apr. 19, 2001

(65) Prior Publication Data

US 2002/0082470 A1 Jun. 27, 2002

Related U.S. Application Data

(60) Provisional application No. 60/240,936, filed on Apr. 27, 2000.

(51) Int. Cl.[7] .................................................. A61F 02/02
(52) U.S. Cl. ......................... 600/37; 128/897; 128/898; 606/201
(58) Field of Search ............................... 600/37; 606/1, 606/201–202; 128/897–898

(56) References Cited

U.S. PATENT DOCUMENTS

| 5,472,438 | A |   | 12/1995 | Schmit et al. ................. 606/1 |
|-----------|---|---|---------|---------------------------------------|
| 5,782,746 | A | * | 7/1998  | Wright ......................... 600/37 |
| 5,799,661 | A |   | 9/1998  | Boyd et al. .................. 128/898 |
| 6,019,722 | A |   | 2/2000  | Spence et al. ............... 600/210 |
| 6,206,827 | B1 |  | 3/2001  | Chin et al. ................... 600/217 |
| 6,251,065 | B1 | * | 6/2001 | Kochamba et al. ........... 600/37 |
| 6,287,250 | B1 |  | 9/2001  | Peng et al. .................... 600/37 |
| 6,328,688 | B1 | * | 12/2001 | Borst et al. .................. 600/37 |
| 6,361,492 | B1 | * | 3/2002 | Santilli ........................ 600/205 |
| 6,364,833 | B1 | * | 4/2002 | Valerio et al. ................ 600/37 |

* cited by examiner

*Primary Examiner*—Robert L. Nasser
(74) *Attorney, Agent, or Firm*—Thomas C. Berry; Daniel W. Latham

(57) ABSTRACT

A suction retractor that provides support to and positions an organ for surgery is provided. This retractor includes a support surface, a plurality of suction elements disposed adjacent the support surface, at least one leash operatively attached to the support surface; and at least one suction tube operatively connected with the suction elements. A method for using the retractor to manipulate an organ during surgery is also provided.

12 Claims, 4 Drawing Sheets

SUCTION RETRACTOR FOR ATTACHING TO AN ORGAN WITHIN A BODY

This application claims the benefit of provisional application No. 60/240,936 filed Apr. 27, 2000.

FIELD OF THE INVENTION

This invention relates to devices that are capable of supporting an organ, such as the heart, and of exposing a given area of tissue to permit a surgical procedure to be performed on the area. In particular, the invention relates to a flexible suction retractor device that is capable of supporting and adjusting an organ so that an area of tissue is exposed for surgery.

BACKGROUND OF THE INVENTION

Surgery on certain vessels in an organ such as the heart is difficult because the vessels are not easily accessible. For example, the circumflex coronary artery lies on the posterior surface of the heart and so the heart must be rotated to access this surface for coronary bypass surgery.

One method of accessing this surface of the heart involves a cardiopulmonary bypass wherein the heart is arrested, the blood drained, an artificial circulatory system is set up for the duration of the procedure and then the heart is lifted and partially rotated. Several methods have been used to support and rotate the heart appropriately. An assistant may hold the heart with outstretched hand but this technique is extremely unwieldy. Artificial metallic "hands" may hold the heart in a similar manner but pose similar disadvantages. A surgical net may be used but the fine strands of the net impinge on the heart and may cause damage. A heart support formed of cloth tapes is described in U.S. Pat. No. 3,983,863 but this support has a rough texture, does not support the heart uniformly and covers areas of the heart from the surgeon's sight. U.S. Pat. No. 4,973,300 describes a cardiac sling that supports the heart uniformly but still covers large areas of the heart and takes up space in the chest cavity.

Because of the risks incurred during cardiopulmonary bypass, other methods have been attempted for performing a coronary artery bypass graft procedure without the cardiac arrest and cardiopulmonary bypass described above. In these methods, an immobilization device is used to immobilize a local area of the heart so that surgery may be performed in that area. One such device and a method for using it are described in U.S. Pat. No. 5,836,311 assigned to Medtronic, Inc., and herein incorporated by reference. For these methods, which localize the surgery, it is even more crucial that the organ be supported and that the area for the surgery be made accessible. The support techniques described above could all be used with such methods of performing a coronary artery bypass graft procedure. However, these techniques continue to have the same disadvantages of being unwieldy, obstructing areas of the heart and possibly causing damage to the heart.

Finally, as endoscopic surgery becomes more prevalent, the area exposed to surgery will become even more localized and the need for supporting the organ and presenting the appropriate surface for surgery will be even greater.

Therefore a device for easily supporting an organ such as the heart during surgery would be desirable. In addition, a device that could appropriately present an area of the organ for surgery without obscuring that area would also be desirable, particularly in an endoscopic surgical procedure. Furthermore, a device that could appropriately support and manipulate the organ during surgery while causing little distress to the organ would also be desirable.

SUMMARY OF THE INVENTION

One aspect of the invention provides for a suction retractor which includes a support paddle, at least one suction element positioned on the support paddle, a suction tube which connects to the section elements, and at least one leash attached to the paddle. The support paddle may be any appropriate paddle or similar support device. The suction elements may be any appropriate suction device, which may be arranged in a variety of configurations. The leash or leashes may be made from a variety of preferably biocompatible materials. The suction tube may also be made from a variety of preferably biocompatible materials. Both leash and suction tube are preferably flexible.

Another aspect of the invention provides a method of exposing a surface of an organ such as the heart using a suction retractor. This method involves positioning the suction elements of the suction retractor adjacent the surface of the organ, communicating a suction to the suction elements, grasping the surface of the organ, and moving the leash to adjust the organ to a desired position.

Another aspect of the invention provides a system for supporting the heart using a suction retractor. This system includes the suction retractor, at least one leash for positioning the suction retractor, a stable object to which one end of the lease may be attached for stability, and a suction source to provide suction to the suction elements which may be used to grasp and support an organ such as the heart.

The foregoing, and other, features and advantages of the invention will become further apparent from the following detailed description of the presently preferred embodiments, read in conjunction with the accompanying drawings. The detailed description and drawings are merely illustrative of the invention rather than limiting, the scope of the invention being defined by the appended claims in equivalence thereof.

DETAILED DESCRIPTION OF THE PRESENTLY PREFERRED EMBODIMENTS

Figure 1:
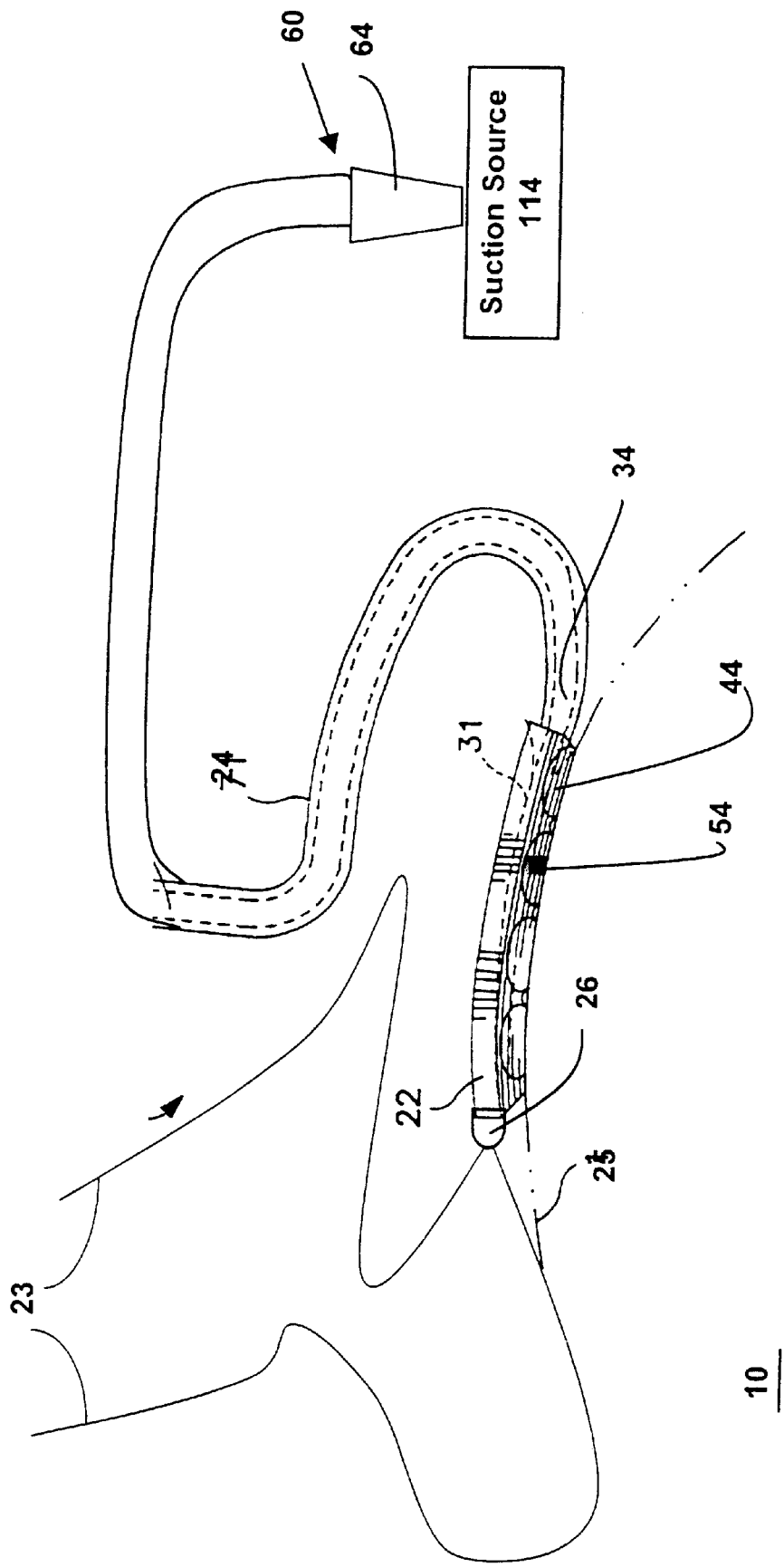
FIG. 1 is a side view of one embodiment of a suction retractor in accordance with the present invention showing its placement against the outline of a heart.

FIG. 1 shows a side view of one preferred embodiment of a suction retractor 10 placed against the outline of a heart 25. The distal end of suction retractor 10 comprises a paddle 22, a plurality of retractor leashes 23 and a flexible suction tube 24. It is contemplated that a sufficiently flexible suction tube 24 could also serve the function of a retractor leash in one embodiment of the invention thus eliminating the need for a separate retractor leash. However, FIG. 1 shows an embodiment of the suction retractor 10 in which suction tube 24 and retractor leashes 23 are separate members.

Paddle 22 may preferably have a generally planar surface that conforms generally to the curvature of a heart 25, shown here in outline. Paddle 22 may also be malleable to conform to a variety of surfaces. Paddle 22 may also be curved. In one preferred embodiment, the retractor leashes 23 serve to provide flexibility and maneuverability to the retractor 10 and are coupled to suction paddle 22 such that suction paddle 22 may be easily placed onto a surface of the heart 25. Although retractor leashes 23 are located at the distal tip of paddle 22 in FIG. 1, it is contemplated that leashes 23 may be attached to any appropriate area of paddle 22. In the embodiment of FIG. 1, leashes 23 are attached to paddle 22 via attachment nub 26. However, it is contemplated that leashes 23 may be attached to paddle 22 by other appropriate means. Meanwhile, suction tube 24 provides suction to the suction retractor 10 via suction conduit 34. This conduit 34 communicates suction to the heart's surface via suction port 44 in paddle 22. A source for creating suction is attached to suction tube 24 at one end 60, preferably by connector 64. This suction source 114 may be, for example, the standard vacuum available in an operating room. The suction source 114 may be coupled to the retractor 10 with a buffer flask (not shown). Suction is provided at a negative pressure of between 200–600 mm Hg with 400 mm Hg preferred.

Preferably, suction paddle 22, retractor leashes 23, suction tube 24 and suction ports 44 are constructed of a biocompatible material. A biocompatible material would prompt little allergenic response and would be resistant to corrosion when placed within the patient's body. Furthermore, the biocompatible material would not cause any additional stress to the patient's body. For example, it would not scrape detrimentally against any elements within the surgical cavity. In one embodiment of the invention, suction paddle 22 may be constructed of stainless steel or a biocompatible rubber. Suction paddle 22 may be colored so that it can be easily visible against the heart. Alternatively, it may be translucent or transparent to provide less obstruction to the surgeon's line of sight. Retractor leashes 23 may be constructed of a silk suture material that is well known in the art. Such material may be a smooth, matte finish polyurethane that is tear-resistant and impervious to blood. The retractor leashes 23 may be translucent or transparent to allow visibility, or may alternatively be colored. In one embodiment of this invention, suction tube 24 is a flexible tube constructed of a soft plastic which may be translucent, transparent or colored. Suction ports 44 may be constructed of biocompatible rubber, which may be translucent, transparent or colored.

In one embodiment, for example, the paddle portion 22 of the retractor 10 may have a width of approximately 3/8 inches and a length of approximately 1¼ inches. The length of suction tube 24 may correspond to the length of the leashes although it may be longer or shorter depending on the length necessary to connect easily to a suction source. Leashes 23 are typically about 18 inches. In one embodiment, for example, the suction ports 44 typically have an outer diameter of 0.240 inches. In one embodiment, for example, suction openings 54 have a rectangular cross section of 0.050×0.030 inches. In another example, suction openings 54 may be circular, with diameter smaller than the diameter of ports 44. In one embodiment the depth of suction ports 44 is from 0.157 inches to 0.118 inches. In one embodiment, openings 54 may be positioned off center of ports 44.

Figure 2:
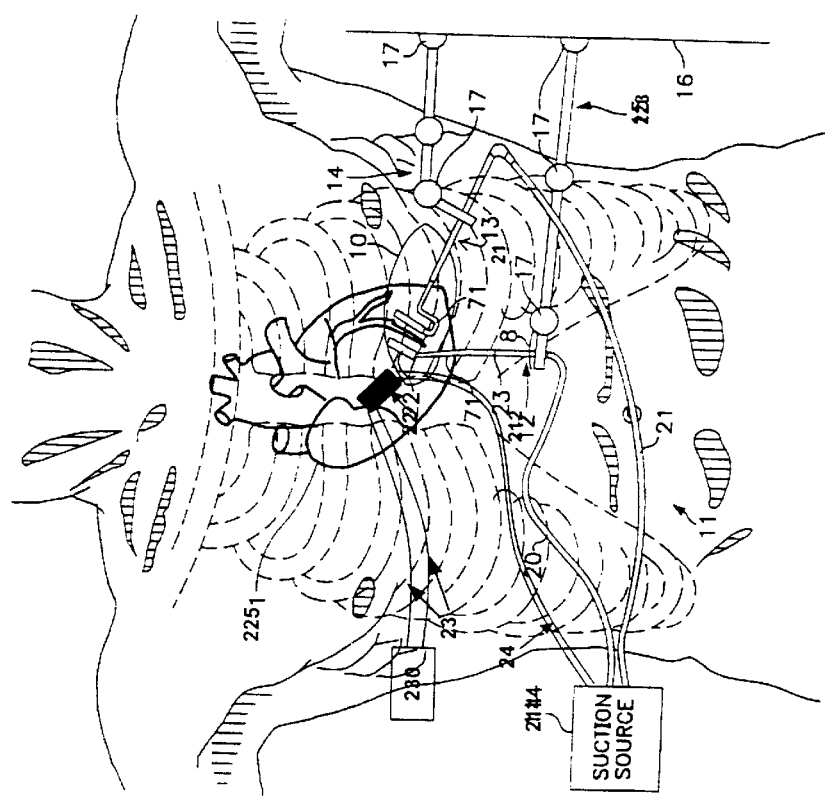
FIG. 2 is a view of an immobilization system, including the suction retractor of FIG. 1, being used to immobilize an area of heart tissue in accordance with the present invention.

Referring to FIG. 2, a system 200 including suction retractor 10 is shown being used to expose and then temporarily immobilize an area of heart tissue for surgery. In one embodiment, surgical access to the local area of heart tissue is achieved through a mini-thoracotomy, preferably performed within either the fourth or fifth intercostal space. An incision of, for example, approximately 10 centimeters is made into the chest cavity between the ribs (seen here in phantom.) The rib cartilage may be temporarily removed and the ribs surrounding the incision slightly spread apart to provide adequate surgical access to the mammary artery and the heart 225.

Suction retractor 10 is then inserted into the cavity and placed adjacent a first surface of the heart 225. It is contemplated that retractor 10 may be covered with a covering during insertion to prevent blood or tissue from clogging the ports 44. However, the arrangement and dimensions of the ports 44 and their openings 54 in the embodiment discussed above dispenses with the need for a cover during insertion.

In either case, once the retractor 10 has been placed adjacent the heart, a suction source 214 then creates suction through the suction tube 24 and ports 44 of the retractor 10 and thereby firmly grasps the heart. It is contemplated that this suction source may be the same source that provides suction for immobilization devices 212, 213, or may be a separate source entirely.

The leashes 23 of the retractor 10 may then be pulled to manipulate the heart 225 into a position where a second surface of the heart is exposed for surgery. These leashes 23 may then be secured using securing devices 223 to a stationary object, such as a surgical table. Other objects that may be used as a stationary object include the chest wall retractor floor, ceiling or even the patient, such as a portion of the skeletal system of the patient, e.g. the sternum. In one embodiment, the free ends of leashes 23 may be attached to a standard suture holder 230.

System 10 further includes a pair of suction devices 212, 213 for immobilizing the heart 225. Once the surface of the heart to be operated upon has been exposed through the use of retractor 10, the suction devices 212, 213 may be introduced.

In an endoscopic surgical procedure, the retractor 10 of the present invention is used in a similar manner to that described above. However, surgical access to a local area of heart tissue in an endoscopic procedure is achieved through an endoscopic port in the sternum. This port is a relatively small hole created by a trocar or needle in the sternum. A cannula or tube may be inserted into this hole and the surgical instruments inserted via the cannula. It is contemplated that the suction retractor 10 of the present invention may be inserted via a cannula into the surgical space and then placed appropriately on a first surface of the heart and manipulated as described above. It is also contemplated that the suction retractor 10 may be attached to the trocar, which creates the hole in the sternum, and thus be inserted in that manner. Refractor 10 may, for example, be disposed within trocar 330, shown in shadow in FIG. 3.

Should the surgeon need to adjust the heart further, the suction may be released, thereby releasing the retractor 10. The suction retractor may then be placed on a new area of the heart, pulled to expose the target area of the heart and then secured as described above.

This is advantageous over other methods of supporting the heart that are less easily re-adjusted.

It is contemplated that suction retractor 10 may be used in a similar manner to support and manipulate organs other than the heart.

Figure 3:
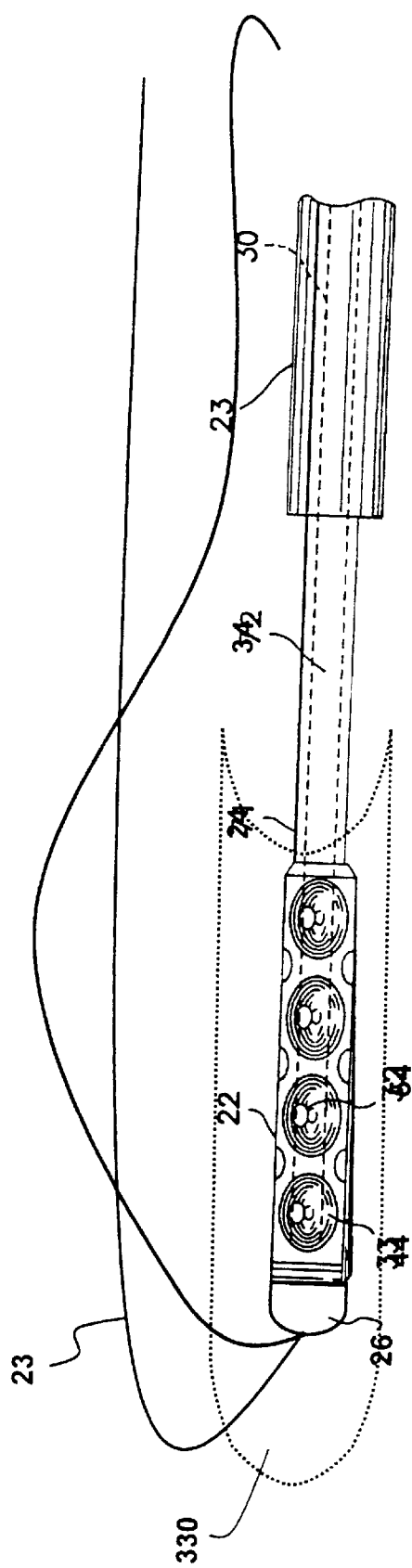
FIG. 3 is a bottom view of the suction retractor of FIG. 1, showing a first configuration of the suction elements.

FIG. 3 is a view of the bottom of suction retractor 10. In this embodiment, the suction ports 44 are arranged, for example, four or five in a row, although the specific or exact number and position used may vary. In one embodiment, for example, each suction port 44 has a suction opening 54, with each opening being located at a position slightly off-center of suction port 44. Suction openings 54 may be positioned off center from suction ports 44 so that if a large upwelling of tissue is caused by the suction (which may occur as a blister or bell-shaped curve) the tissue will not immediately close off the suction by obstructing suction opening 54, as it would if the opening were in the center of suction port 44. In addition, each suction opening 54 has a much smaller diameter as compared to the diameter of suction port 44.

This creates a high resistance pathway between suction port 44 and suction conduit 34. Because of this, loss of a tissue-to-port seal in one suction port (and thus loss of fixation of the suction port to the tissue) does not also cause a precipitous pressure drop in the remainder of the suction ports.

Figure 4:
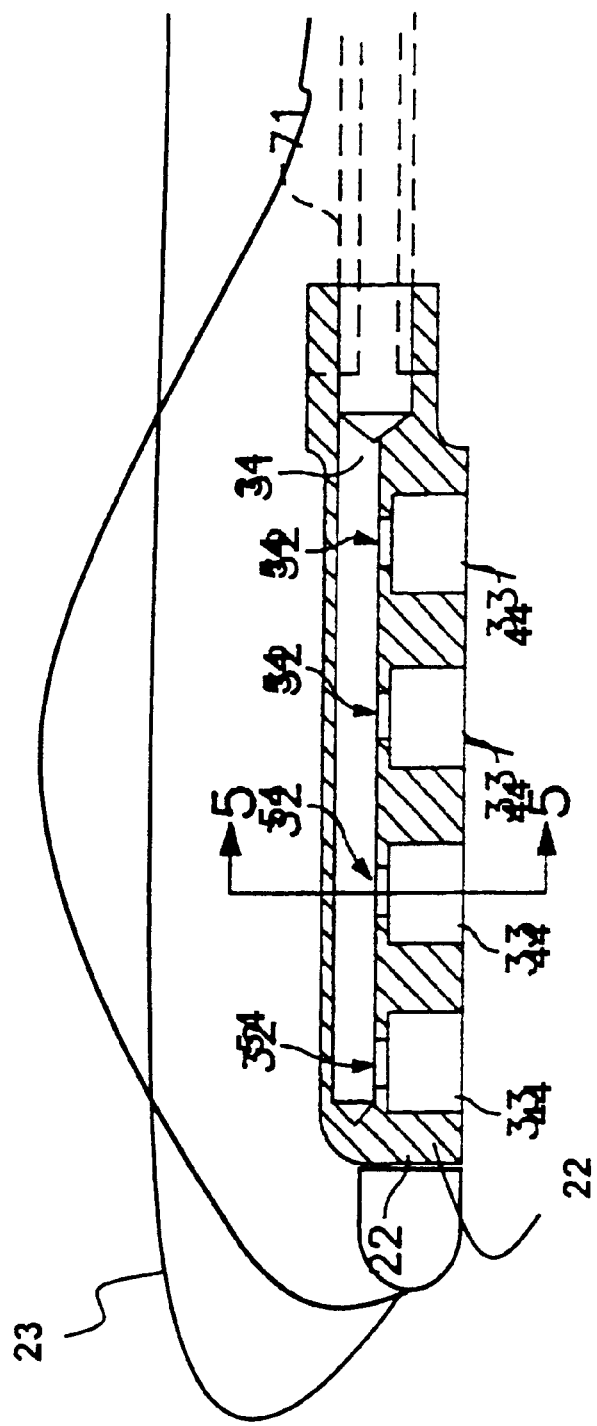
FIG. 4 is a longitudinal cross-sectional view of a suction paddle portion of the retractor of FIG. 1.

FIG. 4 is a longitudinal cross-sectional view of suction paddle 22 used in suction retractor 10. As seen, paddle 22 has a series of suction ports 44 each of which is connected to suction conduit 34 through a suction aperture 54. Each suction port 44 has generally straight, cylindrical sides. Of course other configurations may be used, such as cone-shaped suction ports, dome-shaped suction ports, etc.

It should be appreciated that the embodiments described above are to be considered in all respects only illustrative and not restrictive. The scope of the invention is indicated by the following claims rather than by the foregoing description. All changes that come within the meaning and range of equivalents are to be embraced within their scope.

We claim:

1. A method of exposing a surface of an organ comprising:
   providing a suction retractor device having a support member, at least one suction element disposed adjacent a surface of the support member, and at least one flexible leash having a first end operatively attached to the support member and a second, free end extending away from the support member;
   positioning the at least one suction element adjacent the surface of the organ;
   communicating a suction to the at least one suction element;
   grasping the surface of the organ with the suction; and
   pulling the at least one leash near the second, free end to adjust the organ to a desired position.

2. The method of claim 1 further comprising:
   attaching the second, free end of the leash to a stable object after the organ has been adjusted to a desired position.

3. The method of claim 1 further comprising: p1 accessing the organ via an endoscopic port.

4. The method of claim 3 wherein the endoscopic port is created in the sternum.

5. The method of claim 3 wherein the suction retractor device is introduced through a cannula or tube.

6. The method of claim 2 wherein the leash is secured to a trocar.

7. The method of claim 1 also comprising:
   releasing the suction and releasing the retractor from the surface of the organ
   repositioning the at least one suction element adjacent a second surface of the organ;
   communicating a suction to the at least one suction element;
   grasping the second surface of the organ with the suction; and
   pulling the at least one leash near the second, free end to adjust the organ to a second desired position.

8. A suction retractor for attaching to an organ within a body, comprising:
   a support member having a surface for positioning adjacent the organ;
   at least one suction port positioned on the surface of the support member;
   at least one flexible leash made from suture material operatively attached at a first end to the support member, the flexible leash having a second, free end extending away from the support member that can be pulled to effect movement of the support member and change the position of the organ; and
   at least one suction tube operatively connected to the at least one suction port.

9. A suction retractor for attaching to an organ within a body, comprising:
   a support member having a surface for positioning adjacent the organ;
   at least one suction port positioned on the surface of the support member;
   at least one flexible, translucent leash operatively attached at a first end to the support member, the flexible leash having a second, free end extending away from the support member that can be pulled to effect movement of the support member and change the position of the organ; and
   at least one suction tube operatively connected to the at least one suction port.

10. A suction retractor for attaching to an organ within a body, comprising:
    a support member having a surface for positioning adjacent the organ;
    at least one suction port positioned on the surface of the support member;
    at least one flexible, transparent leash operatively attached at a first end to the support member, the flexible leash having a second, free end extending away from the support member that can be pulled to effect movement of the support member and change the position of the organ; and
    at least one suction tube operatively connected to the at least one suction port.

11. A suction retractor for attaching to an organ within a body, comprising:
    a support member having a surface for positioning adjacent the organ;
    at least one suction port positioned on the surface of the support member;
    at least one flexible leash having a matte finish operatively attached at a first end to the support member, the flexible leash having a second, free end extending away from the support member that can be pulled to effect movement of the support member and change the position of the organ; and
    at least one suction tube operatively connected to the at least one suction port.

12. A suction retractor for attaching to an organ within a body, comprising:
    a support member having a surface for positioning adjacent the organ;
    at least one suction port positioned on the surface of the support member;
    at least one flexible leash having a smooth finish operatively attached at a first end to the support member, the flexible leash having a second, free end extending away from the support member that can be pulled to effect movement of the support member and change the position of the organ; and
    at least one suction tube operatively connected to the at least one suction port.

* * * * *

UNITED STATES PATENT AND TRADEMARK OFFICE
CERTIFICATE OF CORRECTION

PATENT NO. : 6,656,109 B2  Page 1 of 1
APPLICATION NO. : 09/837270
DATED : December 2, 2003
INVENTOR(S) : DeVries et al.

It is certified that error appears in the above-identified patent and that said Letters Patent is hereby corrected as shown below:

Column 5, line 39, claim 3 "comprising: p1 accessing" should read --comprising: accessing--.

Signed and Sealed this

Thirteenth Day of March, 2007

JON W. DUDAS
*Director of the United States Patent and Trademark Office*